(12) United States Patent
Loh et al.

(10) Patent No.: US 9,271,518 B2
(45) Date of Patent: Mar. 1, 2016

(54) MONOGASTRIC ANIMAL FEED

(71) Applicant: UNIVERSITI PUTRA MALAYSIA (UPM), Selangor Darul Ehsan (MY)

(72) Inventors: Teck Chwen Loh, Selangor Darul Ehsan (MY); Hooi Ling Foo, Selangor Darul Ehsan (MY)

(73) Assignee: UNIVERSITI PUTRA MALAYSIA (UPM), Selangor Darul Ehsan (MY)

( * ) Notice: Subject to any disclaimer, the term of this patent is extended or adjusted under 35 U.S.C. 154(b) by 278 days.

(21) Appl. No.: 13/897,138

(22) Filed: May 17, 2013

(65) Prior Publication Data

US 2013/0243908 A1 Sep. 19, 2013

Related U.S. Application Data

(62) Division of application No. 13/144,248, filed as application No. PCT/MY2009/000050 on Apr. 9, 2009.

(51) Int. Cl.
| | |
|---|---|
| C12N 1/20 | (2006.01) |
| A23K 1/18 | (2006.01) |
| A23K 1/00 | (2006.01) |
| C12R 1/25 | (2006.01) |

(52) U.S. Cl.
CPC .............. *A23K 1/1833* (2013.01); *A23K 1/009* (2013.01); *A23K 1/184* (2013.01); *A23K 1/1826* (2013.01); *A23K 1/1846* (2013.01); *A23K 1/1886* (2013.01); *A23K 1/1893* (2013.01); *C12R 1/25* (2013.01)

(58) Field of Classification Search
CPC .............................. A23Y 2220/67; C12R 1/25
See application file for complete search history.

(56) References Cited

U.S. PATENT DOCUMENTS

| | | | |
|---|---|---|---|
| 4,842,871 A | 6/1989 | Hill | |
| 5,895,758 A | 4/1999 | Majnarich et al. | |
| 6,780,447 B2 * | 8/2004 | Raczek | 426/61 |
| 2005/0084500 A1 * | 4/2005 | Molly et al. | 424/195.15 |
| 2007/0172514 A1 * | 7/2007 | Chi et al. | 424/442 |
| 2007/0238148 A1 | 10/2007 | Park et al. | |

FOREIGN PATENT DOCUMENTS

| | | |
|---|---|---|
| DE | 38 41 928 A1 | 6/1990 |
| WO | WO 2005/116188 A | 12/2005 |
| WO | WO 2006/025643 A | 3/2006 |
| WO | WO 2008/143257 A | 11/2008 |

OTHER PUBLICATIONS

U.S. Appl. No. 13/144,248.*
Thanh et al., "Effects of feeding metabolite combinations produced by Lactobacillus plantarum on growth performance, faecal microbial population, small intestine villus height and faecal volatile fatty acids in broilers" *British Poultry Science*, vol. 50, No. 3, 2009, pp. 298-306.
Foo et al., "Screening and characterisation of bacteriocin produced by lactic acid bacteria isolated from Malaysian steamed fish 'ikan rebus'" *Abst. of the General Meeting of the American Society for Microbiology*, vol. 102, 2002, p. 257.
Holo et al., "Plantaricin W from Lactobacillus plantarum belongs to a new family of two-peptide lantibiotics" *Microbiology, Society for General Microbiology*, vol. 147, No. 3, Mar. 1, 2001 pp. 643-651.
Van Reenen et al., "Isolation, purification and partial characterization of plantaricin 423, a baeriocin produced by Lactobacillus plantarum" *J. Appl. Microbiology*, vol. 84, No. 6, Jun. 1, 1998, pp. 1131-1137.
Database EMBL [Online] May 8, 2007, "Lactobacillus plantarum strain BX6-6 16S ribosomal RNA gene, partial sequence." XP002544254, retrieved from accession No. EMBL: EF536363.
Database EMBL [Online] Jun. 13, 2003, "Lactobacillus plantarum gene for 16S ribosomal RNA, partial sequence." XP002544255, retrieved from accession No. EMBL: AB112083.
Okine et al., "Ensiling characteristics of daikon (*Raphanus sativus*) by-product and its potential as an animal feed resource" *Animal Feed Science and Technology*, vol. 136, No. 3-4, Jul. 26, 2007 pp. 248-264.
Loh et al., "Effects on growth performance, faecal microflora and plasma cholesterol after supplementation of spray-dried metabolite to postweaning rats" *Czech Journal of Animal Science*, vol. 54, No. 1, Jan. 2009, pp. 10-16.
Whiter et al. "The Effect of a Dry or Liquid Application of Lactobacillus Plantarum MTD1 on the Fermentation of Alfalfa Silage", *J. of Dairy Science, American Dairy Science Assoc.*, vol. 84, o. 10, Oct. 1, 2001, pp. 2195-2202.
De Angelis et al., "Selection of potential probiotic lactobacilli from pig feces to be used as additives in pelleted feeding" *Research in Microbiology*, vol. 157, No. 8, Oct. 1, 2006 pp. 792-801.
Bucio et al., "Survival of Lactobacillus plantarum 44a after spraying and drying in feed and during exposure to gastrointestinal tract fluids in vitro" *J. of General and Applied Microbiology*, vol. 51, No. 4, Aug. 2005, pp. 221-227.
Loh et al., "Growth Performance and Fecal Microflora of Rats Offered Metabolites from Lactic Acid Bacteria" *J. Applied Animal Research*, vol. 34, No. 1, Sep. 2008, pp. 61-64.

* cited by examiner

*Primary Examiner* — Ruth Davis
(74) *Attorney, Agent, or Firm* — Muncy, Geissler, Olds & Lowe, P.C.

(57) ABSTRACT

The present invention relates an improved feed additive or food supplement formulation obtained from more than one strain of Lactic acid bacteria. The feed additive or supplements is used to feed monogastric animals such as avian, fowl. Moreover, the feed provides better growth and feed utilization for monogastric animals. Further, the animal feed can be used for controlling food intake in the animals.

19 Claims, 3 Drawing Sheets
(3 of 3 Drawing Sheet(s) Filed in Color)

SEQUENCE LISTING

```
<160> NUMBER OF SEQ ID NOS: 5

<210> SEQ ID NO 1
<211> LENGTH: 562
<212> TYPE: DNA
<213> ORGANISM: Lactobacillus plantarum
<220> FEATURE:
<221> NAME/KEY: misc_feature
<223> OTHER INFORMATION: Lactobacillus plantarum strain RG14

<400> SEQUENCE: 1
acgaactctg gtattgattg gtgcttgcat catgatttac atttgagtga gtggcgaact      60
ggtgagtaac acgtgggaaa cctgcccaga agcggggggat aacacctgga aacagatgct     120
aataccgcat aacaacttgg accgcatggt ccgagcttga aagatggctt cggctatcac     180 tttggatgg tcccgcggcg tattagctag atggtggggt aacggctcac catggcaatg      240
atacgtagcc gacctgagag ggtaatcggc cacattggga ctgagacacg gcccaaactc     300
ctacgggagg cagcagtagg gaatcttcca caatggacga aagtctgatg gagcaacgcc     360
gcgtgagtga agaagggttt cggctcgtaa aactctgttg ttaaagaaga acatatctga     420
gagtaactgt tcaggtattg acggtattta accagaaagc cacggctaac tacgtgccag     480
cagccgcggt aatacgtagg tggcaagcgt tgtccggatt tattgggcgt aaagcgagcg     540
caggcggttt tttaagtctg at                                              562

<210> SEQ ID NO 2
<211> LENGTH: 561
<212> TYPE: DNA
<213> ORGANISM: Lactobacillus plantarum
<220> FEATURE:
<221> NAME/KEY: misc_feature
<223> OTHER INFORMATION: Lactobacillus plantarum strain RI-11

<400> SEQUENCE: 2
acgaactctg tattgattgg tgcttgcatc atgatttaca tttgagtgag tggcgaactg      60
```

```
gtgagtaaca cgtgggaaac ctgcccagaa gcggggata  acacctggaa acagatgcta    120
ataccgcata acaacttgga ccgcatggtc cgagcttgaa agatggcttc ggctatcact    180
tttggatggt cccgcggcgt attagctaga tggtgggta  acggctcacc atggcaatga    240
tacgtagccg acctgagagg gtaatcggcc acattggac  tgagacacgg cccaaactcc    300
tacgggaggc agcagtaggg aatcttccac aatggacgaa agtctgatgg agcaacgccg    360
cgtgagtgaa gaagggtttc ggctcgtaaa actctgttgt taaagaagaa catatctgag    420
agtaactgtt caggtattga cggtatttaa ccagaaagcc acggctaact acgtgccagc    480
agccgcggta atacgtaggt ggcaagcgtt gtccggattt attgggcgta aagcgagcgc    540
aggcggtttt ttaagtctga t                                              561

<210> SEQ ID NO 3
<211> LENGTH: 562
<212> TYPE: DNA
<213> ORGANISM: Lactobacillus plantarum

<400> SEQUENCE: 3
acgaactctg gtattgattg gtgcttgcat catgatttac atttgagtga gtggcgaact     60
ggtgagtaac acgtgggaaa cctgcccaga agcgggggat aacacctgga aacagatgct    120
aataccgcat aacaacttgg accgcatggt ccgagcttga agatggcttc ggctatcac    180 ttttggatgg tcccgcggcg tattagctag atggtggggt aacggctcac catggcaatg    240
atacgtagcc gacctgagag ggtaatcggc cacattggga ctgagacacg gcccaaactc    300
ctacgggagg cagcagtagg gaatcttcca caatgggacg aaagtctgat ggagcaacgc    360
cgcgtgagtg aagaaggttt cggctcgtaa aactctgttg ttaaagaaga acatatctga    420
gagtaactgt tcaggtattg acggtattta accagaaagc cacggctaac tacgtgccag    480
cagccgcggt aatacgtagg tggcaagcgt tgtccggatt tattgggcgt aaagcgagcg    540
caggcggttt tttaagtctg at                                             562

<210> SEQ ID NO 4
<211> LENGTH: 562
<212> TYPE: DNA
<213> ORGANISM: Lactobacillus plantarum

<400> SEQUENCE: 4
acgaactctg gtattgattg gtgcttgcat catgatttac atttgagtga gtggcgaact     60
ggtgagtaac acgtgggaaa cctgcccaga agcgggggat aacacctgga aacagatgct    120
aataccgcat aacaacttgg accgcatggt ccgagtttga agatggcttc ggctatcac    180 ttttggatgg tcccgcggcg tattagctag atggtggggt aacggctcac catggcaatg    240
atacgtagcc gacctgagag ggtaatcggc cacattggga ctgagacacg gcccaaactc    300
ctacgggagg cagcagtagg gaatcttcca caatggacga aagtctgatg gagcaacgcc    360
gcgtgagtga agaagggttt cggctcgtaa aactctgttg ttaaagaaga acatatctga    420
gagtaactgt tcaggtattg acggtattta accagaaagc cacggctaac tacgtgccag    480
cagccgcggt aatacgtagg tggcaagcgt tgtccggatt tattgggcgt aaagcgagcg    540
caggcggttt tttaagtctg at                                             562

<210> SEQ ID NO 5
<211> LENGTH: 562
<212> TYPE: DNA
```

```
<213> ORGANISM: Lactobacillus plantarum

<400> SEQUENCE: 5
acgaactctg gtattgattg atgcttgcat catgatttac atttgagtga gtggcgaact      60
ggtgagtaac acgtgggaaa cctgcccaga agcgggggat aacacctgga aacagatgct     120
aataccgcat aacaacttgg accgcatggt ccgagtttga aagatggctt cggctatcac     180
ttttggatgg tcccgcggcg tattagctag atggtggggt aacggctcac catggcaatg     240
atacgtagcc gacctgagag ggtaatcggc cacattggga ctgagacacg gcccaaactc     300
ctacgggagg cagcagtagg gaatcttcca caatggacga aagtctgatg gagcaacgcc     360
gcgtgagtga agaagggttt cggctcgtaa aactctgttg ttaaagaaga acatatctga     420
gagtaactgt tcaggtattg acggtattta accagaaagc cacggctaac tacgtgccag     480
cagccgcggt aatacgtagg tggcaagcgt tgtccggatt tattgggcgt aaagcgagcg     540
caggcggttt tttaagtctg at                                              562
```

MONOGASTRIC ANIMAL FEED

CROSS REFERENCE TO RELATED APPLICATIONS

This application is a Divisional of co-pending application Ser. No. 13/144,248, filed on Jul. 12, 2011, which is a U.S. National Stage of International Application No. PCT/MY2009/000050, filed on Apr. 9, 2009, for which priority is claimed under 35 U.S.C. §120, the entire contents of all of which are hereby incorporated by reference.

FIELD OF INVENTION

The present invention relates to a microbial feed additive for monogastric animal feeds such as poultry, swine and turkeys. More particularly, the present invention relates to the animal feed produced by microorganisms, preferably lactic acid bacteria.

BACKGROUND OF INVENTION

In recent years it has been proposed to use various feed additives to achieve a fast growth in livestock, and in this respect antibiotic additives have attracted the greatest attention. Growth promoting antibiotic is the most common one among feed additives, mainly due to their positive effects in growth or feed conversion efficiency and also reduction of incidence of certain diseases. However, extensive use of antibiotic may cause animals to develop resistance in a number of pathogenic bacteria species (Mikkelsen and Jensen, 2000). Relatively good results have been attained with these additives. More recent findings have shown that such additives give rise to resistant bacteria strains in the livestock and it has also been established that the antibiotic substances are transferred in small amounts to humans. It has also been found that a certain risk exists for hyper sensitiveness in persons who handle such feed. In modern animal farming, various methods have been explored to improve animal health and growth performance. These include better husbandry management, nutrition and utilisation of feed additive. The common feed additives used are antibiotic, probiotics, enzymes and organic acids (Bernardeau et al., 2002). Likewise, cross-resistance may occur to therapeutic antibiotic belongs to the same class of drug, particularly those with close relationships with human antimicrobial therapies. In recent years, it has been proposed to use various feed additives to achieve a fast growth in livestock, and in this respect, antibiotic additives have attracted the greatest attention. It has now been found that by using a feed additive according to the present invention could be an advantage to eliminate the above mentioned disadvantages and still obtain result in livestock production which is at least as good as that previously attained by using antibiotic feed additives. Thus the desired result is obtained without the previous drawbacks.

Some countries already imposed restrictions or prohibitions on the use of antibiotics as growth promoters and this have drawn attention to possible alternatives (Wierup, 2000). During the last few years, research has focused on some valuable strains of lactic acid bacteria (LAB) and their potential use as probiotic agents. Probiotics are considered viable microbial preparations that promote mammalian health by preserving the natural microflora in the intestine. Probiotics are thought to attach to the intestinal mucosa, colonize the intestinal tract and thereby prevent attachment of harmful micro-organisms thereon. A prerequisite for their action resides in that they have to reach the gut's mucosa in a proper and viable form and especially do not get destroyed by the influence of the low pH prevailing in the stomach. In particular, the physiology of the digestive tract of cats and dogs differs from humans. For example, the average pH in the stomach is about 3.4 for dogs and 4.2 for cats. LAB as probiotic are often suggested as alternative for replacing antibiotic. LAB are widely used as starter cultures in meat and meat-products, play a very important role in ensuring the safety of different foods through the production of metabolites such as bacteriocins. Bacteriocins are proteinaceous compounds, which have antimicrobial properties that able to inhibit many different bacterial species, especially pathogenic bacteria (De Vuyst and Vandamme, 1994). These compounds have received a great attention because they are produced by beneficial to human health bacteria and also often used as natural food preservatives. It has been shown that administration of bacteriocins influences the bacterial ecology of the gastrointestinal tract and reduces the levels of pathogenic bacteria in different parts of gastrointestinal tract (van Winsen et al., 2001). Gaenzale et al. (1999) showed that bacteriocin curvacin produced by *Lactobacillus curvatus* inhibited *Escherichia coli* and *Listeria* inoculate in the stomach. It also has been shown that bacteriocins produced by *Lactococcus lactis* subspecies lactis have antibacterial properties (Mishra and Lambert, 1996). U.S. Pat. No. 5,968,569 discloses the inclusion of a probiotic microorganism in a pet food cereal, neither it, nor the remaining available art provides information concerning strains specifically intended for pet health. Thus, there is a need to provide novel bacterial strains that are particularly adapted for pets and that have been selected for their high probiotic properties beneficial for pet health and to incorporate these strains into a pet food composition.

It has been previously known that with the aid of LAB, one can utilize skim milk, buttermilk, and whey as animal feed. The products thus contain, in addition to lactic acid, vitamines, sugar and other carbohydrates but no viable microorganisms. The present invention concerns a growth promoting feed additive containing naturally occurring source of metabolites produced by *Lactobacillus* sp. The invention also relates to the use of an effective amount of metabolites obtained from *Lactobacillus* sp., and providing an optimum dosage of the most effective of metabolites as feed additives for improving the growth performance and overall health of poultry. This animal feed additive shall combine with nutrients to form an animal feed. Scientifically controlled experiments with animals have shown that the economic gain from animals raised on food furnished with additives according to the present invention is increased because the quality and value of the animal products are increased.

SUMMARY OF INVENTION

A preferred embodiment of the present invention relates to a biologically pure culture of a probiotic bacteria strain, wherein the bacteria strain is a lactic acid bacteria selected from the group consisting of *Lactobacillus plantarum* (preferably RI11, RG14, RS5 and RG11 strains). It is said that the lactic acid bacteria, is capable of producing metabolites including bacteriocins. The present invention discloses, the metabolites are added into animal feed as an additive and/or supplement. The animal feed comprises an effective amount of 0.1% to 0.5% metabolites of dry weight.

Accordingly, the animal feed includes; nutrients, bacteriocins, vitamin (preferably vitamin B), organic acids (preferably formic acid, acetic acid and lactic acid) and/or combinations thereof. Moreover, the animal feed includes a combination of bacteriocins, and organic acids or a combination of bacteriocins, vitamin B and organic acids. The bacteriocins used in this particular animal feed is preferably between 0.05% and 0.8%.

In addition, the present invention relates to animal feed formulation including corn; meal; rice bran; wheat pollard; molasses; palm oil, crude coco oil; limestone; monodicalciumphosphate; dicalcium phosphate; salt; lysine; choline chloride; vitamins; minerals; threonine; anti-mold compounds; copper sulfate; DL-methionine; anti-oxidants.

Preferably, the corn used is yellow corn, the meal used includes soybean and copra meal, the palm oil used includes refined and crude palm oil. Additionally, the formulation further includes any of the combination selected from the group of yellow corn; soybean meal; copra meal; rice bran; molasses; crude coco oil; limestone; salt; lysine; choline chloride; vitamins; minerals; threonine; anti-mold compounds; copper sulfate; DLmethionine; and anti-oxidants.

In particular, the animal feed formulation further includes metabolites such as bacteriocins, combine with vitamin II, and organic acids. It is suggested, the metabolites are added into the animal feed amounting between 0.5 and 8 kg of the total feed ration.

More particularly, the animal feed formulation provides the means to increase a total feed intake between 3% and 10% and the formulation provides an increase to an animal growth between 5% and 7%. Accordingly, the animal feed formulation provides a conversion rate between 3% and 8%.

In a preferred embodiment of the present invention relates to an animal feed formulation providing the capability to reduce faecal enterobacteriaceae count and increase faecal lactic bacteria count in monogastric or non-ruminant animals. Accordingly, the formulation also provides the capability to reduce plasma and meat cholesterol in monogastric or non-ruminant animals. The formulation also provides the capability to increase villi height of small intestine in monogastric or non-ruminant animals.

Accordingly, the present invention relates to a process for promoting growth and/or feed conversion in a monogastric or non-ruminant animal, wherein the process comprising feeding the animal an effective amount of bacteriocins, mixed with vitamin B, and organic acids.

In another embodiment of the present invention relates to animal feed containing metabolites produced by *Lactobacillus plantarum* (preferably RI11, RG14, RS5 and RG11 strains).

Yet, another embodiment of the present invention relates to the use of the animal feed for monogastric animal/s, (preferably avian, is rabbit, mink, chinchilla, dog, rodent, a swine, or a preruminant calf or a preruminant lamb).

BRIEF DESCRIPTION OF DRAWINGS

The patent or application file contains at least one drawing executed in color. Copies of this patent or patent application publication with color drawing(s) will be provided by the Office upon request and payment of the necessary fee.

The accompanied drawings constitute part of this specification and include an exemplary or preferred embodiment of the invention, which may be embodied in various forms. It should be understood, however, the disclosed preferred embodiments are merely exemplary of the invention. Therefore, the figures disclosed herein are not to be interpreted as limiting, but merely as the basis for the claims and for teaching one skilled in the art of the invention.

DETAILED DESCRIPTION OF THE INVENTION

Figure 1A:
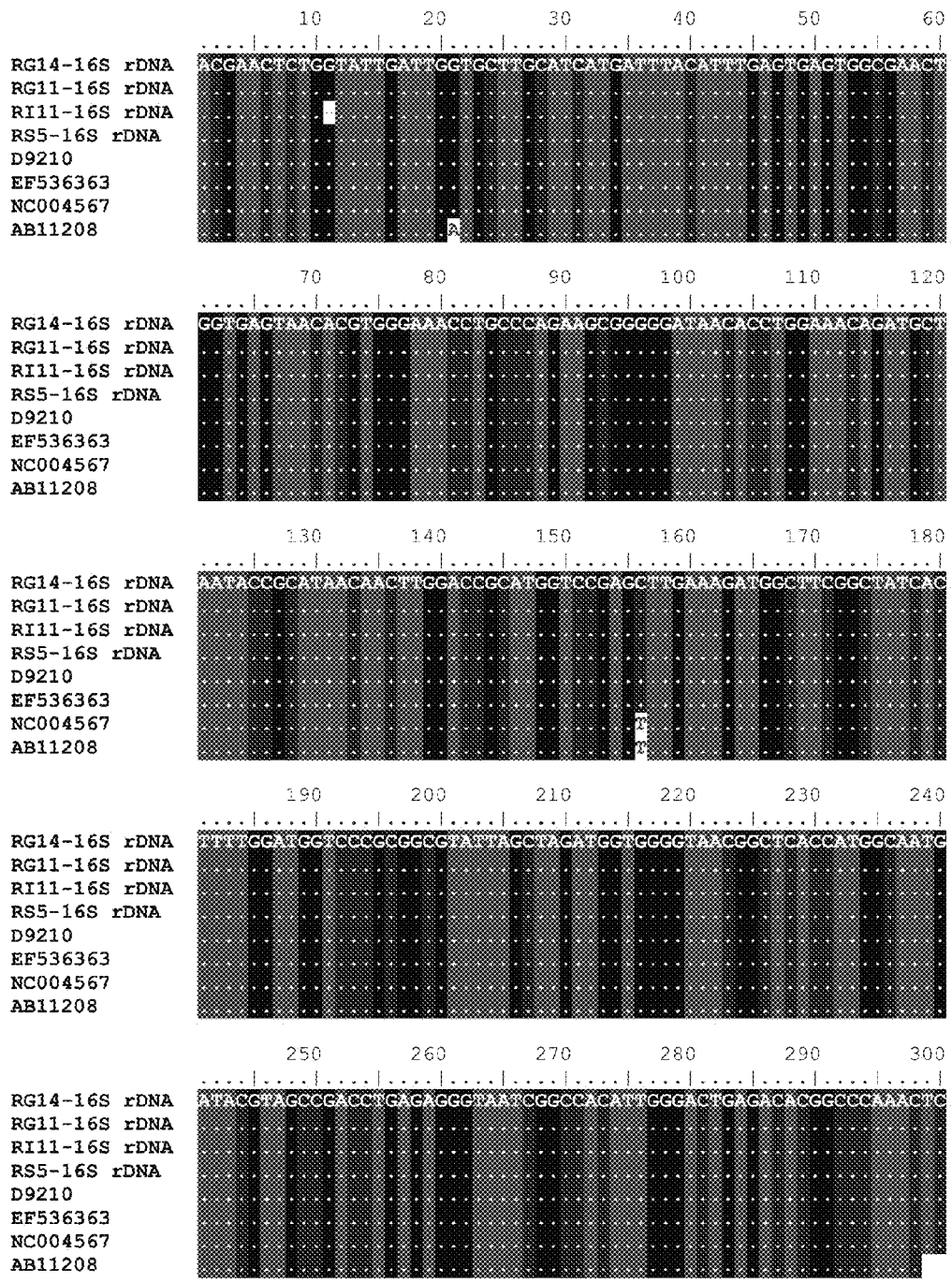
FIGS. 1A and 1B show 16S rDNA partial sequence alignments for the strains RG14 (SEQ ID NO: 1), RG11, RI11 (SEQ ID NO: 2) and RS5 together with four available sequences in GenBank (Accession numbers: D9210, EF536363 (SEQ ID NO: 3), NC004567 (SEQ ID NO: 4) and AB11208 (SEQ ID NO: 5)).
Figure 1B:
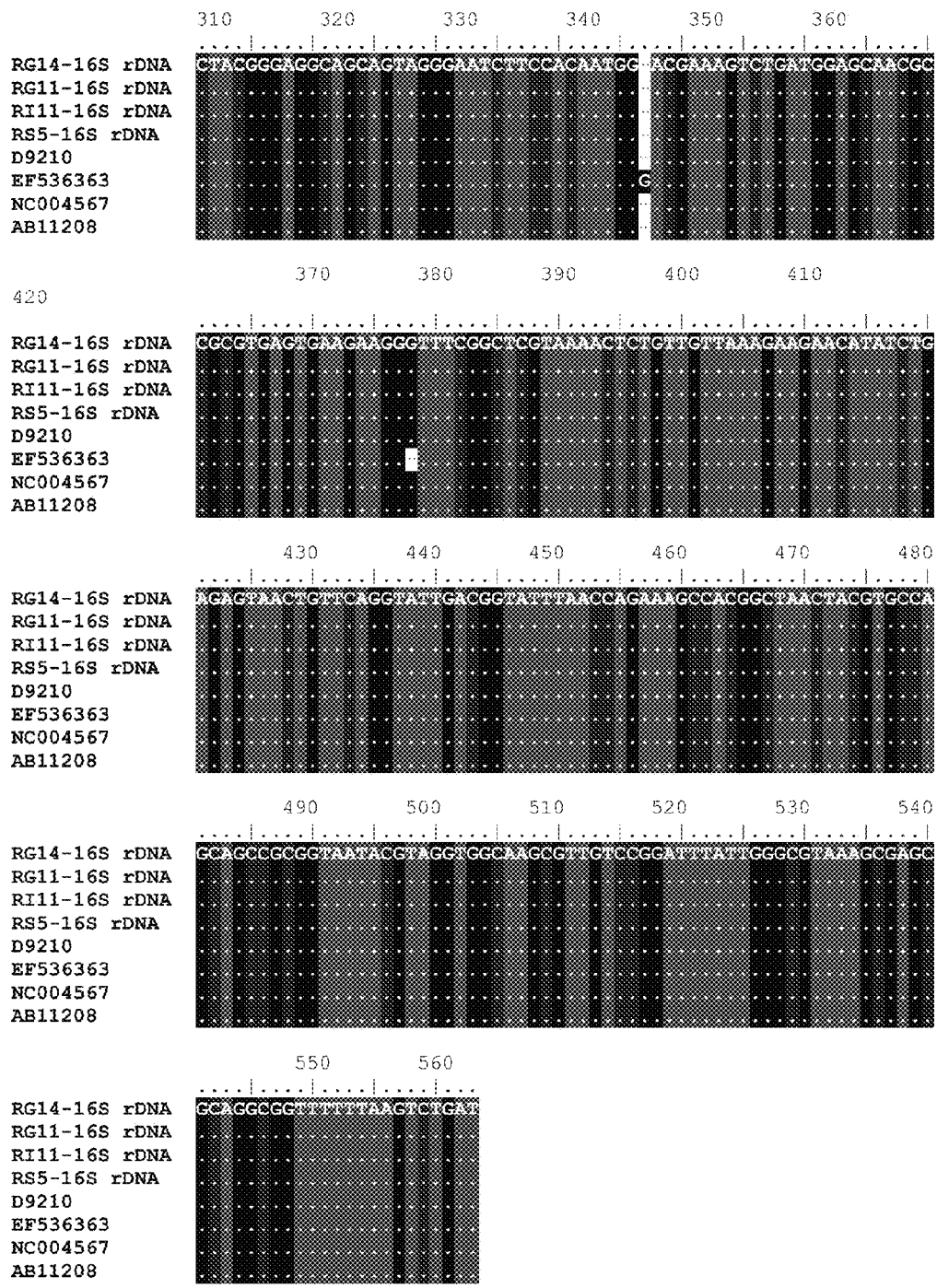
Figure 2:
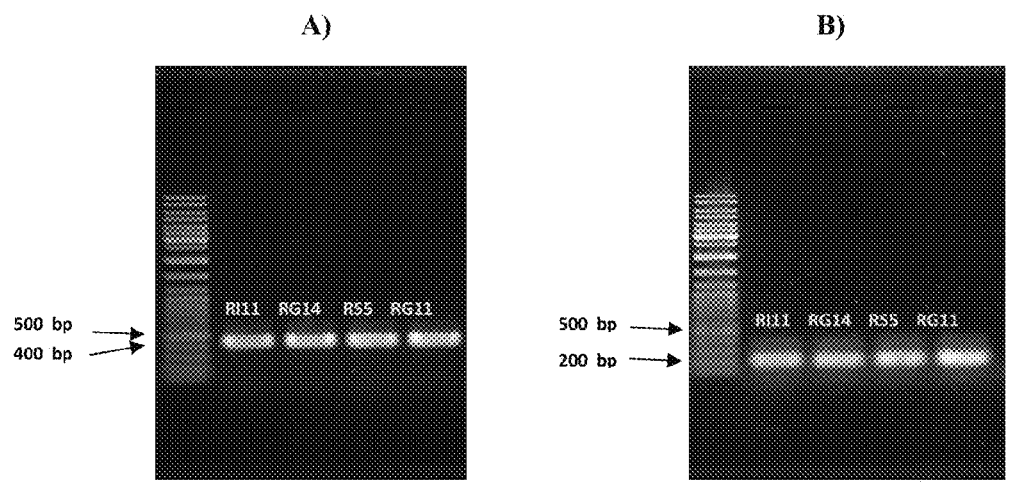
FIG. 2 shows amplification of bacteriocin structural genes from *L. plantarum* strains. A' Amplification of *Plantaricin EF* (~450 bp). B) Amplification of *Plantaricin W* (~200 bp).

A detailed description of preferred embodiments of the invention is disclosed herein. It should be understood, however, the disclosed preferred embodiments are merely exemplary of the invention, which may be embodied in various forms. Therefore, the details disclosed herein are not to be interpreted as limiting, but merely as the basis for the claims and for teaching one skilled in the art of the invention.

A preferred embodiment of the present invention provides methods for improving animal agriculture, in particular in the production of meat producing livestock such as poultry. The methods for provides a feed strategy by having the capability to improve the followings; growth performance, carcass composition, appearance, and overall animal health. For example, it is said to illustrate that the methods of the present invention shows an improve of any one or combination of the following: animal production performance (including growth performance, faecal microflora, volatile fatty acids and villi height of small intestine); plasma cholesterol; and use of dietary nutrients.

Yet, the object of the present invention relates to the effects of the metabolites produced by *Lactobacillus* sp. within the growth performance, faecal microbial population, small intestine villus height and faecal volatile fatty acids (VFA) in broilers chickens.

Yet, another object of the present invention provides the means to identify an optimal combination of the *Lactobacillus* sp. metabolites as an additive or supplementation in the diets of monogastric animals. Accordingly, an optimal dosage is preferred for metabolite combination in animal feed additive or supplementation in the diets of monogastric animals.

The present invention also provides the means for the metabolites to possess probiotic characteristics. This could give the means to improve the animals overall health. It is another object of the present invention; the animal feed additive helps an animal to further digest its food. Accordingly, the animal feed provides an advantage by limiting odour from the animal's manure and providing a fine quality of manure in an agricultural land.

BEST MODE TO CARRY OUT THE INVENTION

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. It must be noted that as used herein and in the appended claims, the singular forms "a," "an," and "the" include plural referents unless the context clearly dictates otherwise.

Monogastric animals such as pigs, poultry veal calves and fish are grown intensively for the production of meat, fish and eggs. These animals are fed diets containing a variety of raw materials of animal and/or vegetable origin to supply energy and protein. Most of the feed that is consumed is produced commercially, but a significant part is produced on the farm and fed directly. The feed is often supplemented with vitamins and minerals to meet the animal's nutrient requirements.

The present invention provides novel metabolites possessing probiotic characteristics for use as feed additive or growth promoter in poultry. An animal feed additive that includes an effective amount of a naturally occurring source of *Lactobacillus* sp metabolites is provided. Moreover, the present invention relates to a biologically pure culture of *Lactobacillus plantarum* RS5, R11, RG14 and RG11 (Comb 3456) or a mutant thereof obtained from a microorganism. The microorganisms were deposited at Agricultural Research Culture Collection (NRRL) located at 1815 N. University Street, Peoria, Ill. 61604 on Jun. 18, 2015. *Lactobacillus plantarum* strains RS5, RI11, RG14 and RG11 are deposited under accession numbers NRRL B-67069, NRRL B-67072, NRRL B-67071, and NRRL B-67070, respectively. Preferably, the biologically pure culture of *plantarum* RS5, R11, RG14 and RG11 or a mutant thereof is capable of producing an effective amount of metabolites for the use as an animal feed.

Preferably, the animal feed additive includes at least about 0.2% (w/v) metabolites in combination on a dry weight basis. This animal feed additive may be combined with nutrients to form an animal feed, which is another aspect of the present invention. Still further, the present invention includes a method of feeding animals the animals feed. The subject invention provides methods for improving poultry health. In specific embodiments, the invention provides methods for accelerating and/or augmenting poultry growth; improving immunity; and overall health of poultry. To do so, the present invention provides materials and methods for administering metabolites of *Lactobacillus* sp isolated from Malaysian foods to poultry.

Four combinations of metabolites produced from strains of *L. plantarum* were used to study the performance of broiler chickens. A total of 432 male Ross broilers were raised from day old to 42 days of age in deep litter house pens (12 birds/pen). These birds were divided into 6 groups and fed with different diets: (i) standard corn-soybean based diet (negative control); (ii) standard corn-soybean based diet+ Neomycin and Oxytetracycline (positive control); (iii) standard corn-soybean based diet+0.3% metabolite combination of *L. plantarum* RS5, RI11, RG14 and RG11 strains (com3456); (iv) standard corn-soybean based diet+0.3% metabolite combination of *L. plantarum* TL1, RI11 and RG11 (Com246); (v) standard cornsoybean based diet+0.3% metabolite combination of *L. plantarum* TL1, RG14 and RG-11 (Com256) and (vi) standard corn-soybean based diet+ 0.3% metabolite combination of *L. plantarum* TL1, RS5, RG14 and RG11 (Com2356). Higher final body weight, weight gain, average daily gain and lower feed conversion ratio were significantly (P<0.05) found in all four treated groups. Metabolites combination supplementation also increased faecal LAB population, small intestine villus height and faecal volatile fatty acids and lowered cholesterol and faecal Enterobacteriaceae population. The effects of feeding different dosages of metabolite combination of *L. plantarum* RS5, RI11, RG14 and RG11 strains (Com3456) on the performance of broiler chickens was studied. A total of 504 male Ross broilers were grouped into 7 treatments and offered with different diets: (i) standard corn-soybean based diet (negative control); (ii) standard comsoybean based diet+ 100 ppm neomycin and oxytetracycline (positive control); (iii) standard corn-soybean based diet+0.1% metabolite combination of *L. plantarum* RS5, RI11, RG14 and RG11 strains (Com3456); (iv) standard corn-soybean based diet+0.2% of Com3456; (v) standard corn-soybean based diet+0.3% of Com3456 (vi) standard corn-soybean based diet+0.4% of Com3456 and (vii) standard corn-soybean based diet+0.5% of Com3456. Supplementation of Com3456 with different dosages improved growth performance, reduced Enterobacteriaceae and increased lactic acid bacteria count, and increased villi height of small intestine and faecal volatile fatty acids concentration. Treatment with 0.4% and 0.2% Com3456 had the best results, especially in terms of growth performance; feed conversion ratio and villi height among other dosages. However, the dosage of 0.2% was recommended due to its lower concentration with similar effect as 0.4%. These results indicate that 0.2% is an optimum level to be included in the diets of broiler in order to replace antibiotic growth promoters.

EXAMPLES

Broiler Chicks and Experimental Design

A total of 432 male Ross broilers from local company were raised from day old to 42 days of age in deep litter house. Each pen consisted of 12 birds and was randomly allocated to the open house with wood shavings litter. Upon arrival, the birds were vaccinated against infectious bronchitis (IB) and Newcastle disease (ND) (IB-ND Fort Dodge, USA) by intraocular route. The IBD vaccine (UPM93, MyVac, Malaysia) against infectious bursal disease IBI) was applied on day 14 of the rearing period. After vaccination, the birds were wing banded for monitoring of individual weight, water and feed were provided ad libitum. The starter and finisher diets were offered to the birds from 0-21 and 22-42 days of age, respectively. The dietary treatments consisted of: (i) corn-soybean basal diet without antibiotic (−ve control); (ii) basal diet with 100 ppm neomycin and oxytetracycline (+ve control); (iii) basal diet supplemented with 0.1% of metabolite combination from 4 strains of *L. plantarum* RS5, RI11, RG14 and RG11 (Com3456); (iv) basal diet supplemented with 0.2% metabolite combinations of Com3456; (v) basal diet supplemented with 0.3% metabolite combinations of Com3456; (vi) basal diet supplemented with 0.4% metabolite combinations of Com 3456 and (vii) basal diet supplemented with 0.5% metabolite combination of Com3456. The diets were formulated to meet the requirements of all nutrients for broiler chickens. The percentage composition of starter and finisher diets are presented in Tables 1 and 2, respectively

TABLE 1

Percentage composition of starter diet

| Ingredients | Dietary Treatments[1] | | | | | |
|---|---|---|---|---|---|---|
| | −ve Control | +ve Control | Com3456 | Com246 | Com256 | Com2456 |
| Corn | 50.600 | 50.600 | 50.600 | 50.600 | 50.600 | 50.600 |
| Soybean | 29.382 | 29.382 | 29.382 | 29.382 | 29.382 | 29.382 |
| Wheat Pollard | 6.072 | 6.062 | 5.772 | 5.772 | 5.772 | 5.772 |
| CPO | 3.600 | 3.600 | 3.600 | 3.600 | 3.600 | 3.600 |
| Fish Meal 55% | 7.600 | 7.600 | 7.600 | 7.600 | 7.600 | 7.600 |
| L-Lysine | 0.250 | 0.250 | 0.250 | 0.250 | 0.250 | 0.250 |
| DL-Methionine | 0.200 | 0.200 | 0.200 | 0.200 | 0.200 | 0.200 |
| Monodicalciumphosphate 21 | 1.000 | 1.000 | 1.000 | 1.000 | 1.000 | 1.000 |
| Calcium carbonate | 0.680 | 0.680 | 0.680 | 0.680 | 0.680 | 0.680 |
| Choline chloride | 0.060 | 0.060 | 0.060 | 0.060 | 0.060 | 0.060 |
| Salt | 0.250 | 0.250 | 0.250 | 0.250 | 0.250 | 0.250 |
| Mineral Mix[2] | 0.100 | 0.100 | 0.100 | 0.100 | 0.100 | 0.100 |
| Vitamin Mix[3] | 0.060 | 0.060 | 0.060 | 0.060 | 0.060 | 0.060 |
| Antioxidant | 0.010 | 0.010 | 0.010 | 0.010 | 0.010 | 0.010 |
| Toxinbinder | 0.135 | 0.135 | 0.135 | 0.135 | 0.135 | 0.135 |
| Antibiotic[4] | | 0.010 | | | | |
| Metabolite powder | | | 0.300 | 0.300 | 0.300 | 0.300 |
| Total | 100 | 100 | 100 | 100 | 100 | 100 |
| Calculated analysis: | | | | | | |
| Crude protein, % | 22.50 | 22.48 | 22.48 | 22.47 | 22.45 | 22.44 |
| ME, kCal/kg | 2919.90 | 2918.68 | 2918.68 | 2917.48 | 2916.28 | 2915.08 |

[1]Com3456 is a combination of 4 strains RS5, RI11 RG11 and RG14; Com246 is a combination of TL1, RI11 and RG11; Com256 is a combination of TL1, RI14 and RG11; Com2456 is a combination of TL1, RI11, RG14 and RG11.
[2]Mineral mix that provided per kilogram of the diet: Fe 100 mg; Mn 110 mg; Cu 20 mg; Zn 100 mg; I 2 mg; Se 0.2 mg; Co 0.6 mg.
[3]Vitamin mix that provided per kilogram of the diet: Vitamin A 6,667 IU; vitamin D 1,000 IU; vitamin E 23 IU; vitamin K3 1.33 mg; cobalamin 0.03 mg; Thiamin 0.83 mg; riboflavin 2 mg; folic acid 0.33 mg; biotin 0.03 mg; pantothenic acid 3.75 mg; niacin 23.3 mg; pyridoxine 1.33 mg.
[4]a combination of oxytetracyclin and neomycin at the concentration of 100 ppm (w/w).

TABLE 2

Percentage composition of finisher diet

| Ingredients | Dietary Treatments[1] | | | | | |
|---|---|---|---|---|---|---|
| | −ve Control | +ve Control | Com3456 | Com246 | Com256 | Com2456 |
| Corn | 54.900 | 54.900 | 54.900 | 54.900 | 54.900 | 54.900 |
| Soybean | 26.900 | 26.900 | 26.900 | 26.900 | 26.900 | 26.900 |
| Wheat Pollard | 6.375 | 6.365 | 6.075 | 6.075 | 6.075 | 6.075 |
| CPO | 3.200 | 3.200 | 3.200 | 3.200 | 3.200 | 3.200 |
| Fish Meal 55% | 5.000 | 5.000 | 5.000 | 5.000 | 5.000 | 5.000 |
| L-Lysine | 0.250 | 0.250 | 0.250 | 0.250 | 0.250 | 0.250 |
| DL-Methionine | 0.200 | 0.200 | 0.200 | 0.200 | 0.200 | 0.200 |
| Monodicalciumphosphate 21 | 1.400 | 1.400 | 1.400 | 1.400 | 1.400 | 1.400 |
| Calcium carbonate | 0.992 | 0.992 | 0.992 | 0.992 | 0.992 | 0.992 |
| Choline chloride | 0.058 | 0.058 | 0.058 | 0.058 | 0.058 | 0.058 |
| Salt | 0.250 | 0.250 | 0.250 | 0.250 | 0.250 | 0.250 |
| Mineral Mix[2] | 0.100 | 0.100 | 0.100 | 0.100 | 0.100 | 0.100 |
| Vitamin Mix[3] | 0.058 | 0.058 | 0.058 | 0.058 | 0.058 | 0.058 |
| Antioxidant | 0.008 | 0.008 | 0.008 | 0.008 | 0.008 | 0.008 |
| Toxinbinder | 0.150 | 0.150 | 0.150 | 0.150 | 0.150 | 0.150 |
| Antibiotic[4] | | 0.010 | | | | |
| Metabolite powder | | | 0.300 | 0.300 | 0.300 | 0.300 |
| Total | 100 | 100 | 100 | 100 | 100 | 100 |
| Calculated analysis: | | | | | | |
| Crude protein, % | 20.34 | 20.34 | 20.29 | 20.29 | 20.29 | 20.29 |
| ME, kCal/kg | 2912.30 | 2912.20 | 2908.60 | 2908.60 | 2908.60 | 2908.60 |

[1]Com3456 is a combination of 4 strains RS5, RI11 RG11 and RG14; Com246 is a combination of TL1, RI11 and RG11; Com256 is a combination of TL1, RI14 and RG11; Com2456 is a combination of TL1, RI11, RG14 and RG11.
[2]Mineral mix that provided per kilogram of the diet: Fe 100 mg; Mn 110 mg; Cu 20 mg; Zn 100 mg; I 2 mg; Se 0.2 mg; Co 0.6 mg.
[3]Vitamin mix that provided per kilogram of the diet: Vitamin A 6,667 IU; vitamin D 1,000 IU; vitamin E 23 IU; vitamin K3 1.33 mg; cobalamin 0.03 mg; Thiamin 0.83 mg; riboflavin 2 mg; folic acid 0.33 mg; biotin 0.03 mg; pantothenic acid 3.75 mg; niacin 23.3 mg; pyridoxine 1.33 mg.
[4]a combination of oxytetracyclin and neomycin at the concentration of 100 ppm (w/w).

Data and Sample Collection

The individual body weight (BW) and pen feed intake (FI) were recorded weekly and live weight gain (WG), feed conversion ratio (FCR) and average daily gain (ADG) were calculated. Twelve birds at week 6 of each treatment group were randomly and equally selected and slaughtered for sampling as feces and small intestines were taken for further analysis. All procedures were approved by Research Advisory Committee, University Putra Malaysia.

Growth Performance

The growth performance is shown in Table 3. The BW, total WG and ADG of chickens at 42 days of age in the −ve control treatment were the lowest (p<0.05) among the treatments, while the chickens in treatment, supplemented with 0.4% Com3456 from 4 strains of L. plantarum had the highest (p<0.05) BW, WG and ADG at 6 weeks of age, followed by birds of +ve control and 0.2% Com3456 at the third place. However, there was no BW and WG difference (p>0.05) among chickens in +ve control and treatments supplemented with Com3456, except for treatment supplemented with 0.5% Com3456, which was the lowest among treated groups. Feed intake means were not significantly different (p>0.05) among the treatments. Relating to the FCR, the lowest result (p<0.05) was found in treatment supplemented with 0.4% Com3456 as compared with the remaining of the treatments. It shown that higher live BW, total WG and ADG for +ve control and 5 groups supplemented with different dosages of Com3456 compared to that of birds in −ve control, which was fed with corn-soybean based diet. The metabolite combinations from the 4 strains of L. plantarum (Com3456) at different levels of dosages could partially replace antibiotic growth promoter and the optimal dosage in terms of growth performance was 0.4% Com3456, which gave the highest growth performance, followed by 0.2% Com3456. In terms of improvement percentage of performance compared to −ve control, birds supplemented with different dosages of metabolite combinations had 4-12% higher live BW at week 6 than −ve control birds.

The metabolite combinations as potential replacement of AGP are due to their antimicrobial effects. The main effects of antimicrobials in improving growth rate were due to its bacteriostatic and bactericidal effect to inhibit and kill pathogenic bacterial load in gastrointestinal microflora. The antibacterial activity of AGP has been proven in germ free animals.

Faecal Lactic Acid Bacteria and Enterobacteriaceae Count (ENT)

The faecal LAB and ENT population was determined using the method as described by Foo et al. (2003b). Ten percent (w/v) of faecal sample was diluted in sterile peptone water, left at room temperature for an hour prior to further tenfold serial dilutions (v/v). Enumerations of LAB were performed on MRS-agar (Lactobacillus-Agar De Man, ROGOSA and SHAPE) (Merck®, KgaA, Darmstadt). The plates were incubated in anaerobic jar at 30° C. for 48 hours. ENT were spread and counted on EMB-Agar (Eosin-methylene-blue Lactose Sucrose Agar (Merck®, KgaA, Darmstadt) and incubated aerobically for 24 hours at 37° C. The number of colony-forming units (CFU) was expressed as the base 10 logarithm of CFU (log CFU) per gram. All samples were repeated in triplicates. Faecal LAB and ENT count is presented in Table 4. The faecal LAB count from −ve control birds was the lowest (p<0.05), while no significant difference was found among the remaining of the treatments. With regard to ENT count at week 6, the −ve and +ve control birds had the highest (p<0.05) results. In contrast, the lowest (p<0.05) ENT count was observed in 0.2% and 0.5% Com3456. ENT count from other treated groups of 0.1%, 0.3% and 0.4% Com3456 were also significantly lower (p<0.05) than that of −ve and +ve control.

It is shown that the effect of metabolite combinations in reducing gastrointestinal ENT. Additionally, the metabolite combinations increased gastrointestinal LAB. Although with different degrees, all dosage levels of metabolite combinations had effects in increasing gastrointestinal LAB. All treatments supplemented with Com3456 had positive effects in reducing ENT count. The effect of metabolite combination in reducing gastrointestinal ENT gave better chances for LAB to increase their population in intestinal microflora via competitive exclusion.

TABLE 3

Growth performance at week 6 of treatments supplemented with different metabolite combinations

| Parameter | Dietary Treatments[1] | | | | | | |
|---|---|---|---|---|---|---|---|
| | −ve Control | + ve Control | Com3456 | Com246 | Com256 | Com2456 | SEM |
| Feed intake, kg | 4.38 | 4.38 | 4.45 | 4.4 | 4.21 | 4.46 | 0.04 |
| Average daily gain, g | 49.40$^b$ | 53.28$^a$ | 53.43$^a$ | 52.59$^a$ | 52.53$^a$ | 52.99$^a$ | 0.36 |
| Body weight, kg | 2.07$^b$ | 2.22$^a$ | 2.23$^a$ | 2.20$^a$ | 2.20$^a$ | 2.21$^a$ | 0.01 |
| Total weight gain, kg | 2.03$^b$ | 2.18$^a$ | 2.19$^a$ | 2.16$^a$ | 2.15$^a$ | 2.17$^a$ | 0.01 |
| Feed conversion ratio | 2.17$^a$ | 2.01$^b$ | 2.04$^b$ | 2.06$^b$ | 1.98$^b$ | 2.05$^b$ | 0.02 |

$^{a,b}$Means ± SEM in the same row with common superscript are non-significantly different.
[1]Com3456 is a combination of 4 strains RS5, RI11 RG11 and RG14; Com246 is a combination of TL1, RI11 and RG11; Com256 is a combination of TL1, RI14 and RG11; Com2456 is a combination of TL1, RI11, RG14 and RG11.

TABLE 4

Faecal LAB and ENT count and volatile fatty acids of treatments supplemented with different metabolite combinations

| Parameters | −ve control | +ve control | Com3456 | Com246 | Com256 | Com2456 | SEM |
|---|---|---|---|---|---|---|---|
| Microbial count, logCFU/g | | | | | | | |
| LAB | 5.78[c] | 5.92[bc] | 6.63[a] | 6.26[ba] | 6.42[a] | 6.40[a] | 0.06 |
| ENT | 3.83[a] | 3.74[ab] | 3.10[c] | 3.25[bc] | 3.65[bac] | 3.57[bac] | 0.08 |
| Volatile fatty acids, mM | | | | | | | |
| Acetic | 33.16[b] | 54.80[ba] | 65.72[a] | 47.61[ba] | 50.76[ba] | 63.80[ba] | 4.16 |
| Propionic | 1.18[c] | 5.22[bc] | 3.30[bc] | 13.18[a] | 6.07[bac] | 9.73[ba] | 1.07 |
| Butyric | 1.41[b] | 5.33[ba] | 2.45[ba] | 7.83[a] | 3.44[ba] | 6.36[ba] | 0.81 |
| Others | 0.60[b] | 2.04[ba] | 1.34[ba] | 2.40[a] | 1.18[ba] | 1.96[ba] | 0.23 |
| Total | 36.34[b] | 67.40[ba] | 72.50[a] | 69.80[ba] | 61.40[ba] | 81.80[a] | 5.57 |

[a-c]Row means ± SEM with common small superscripts are non-significantly different.
[1]Com3456 is a combination of 4 strains RS5, RI11 RG11 and RG14; Com246 is a combination of TL1, RI11 and RG11; Com256 is a combination of TL1, RI14 and RG11; Com2456 is a combination of TL1, RI11, RG14 and RG11.

Small Intestine Morphology

The procedure was a modified method as described by Hair-Bejo (1990). Segments of 5 to 6 cm long were removed from the duodenum, jejunum, and ileum as follows: i) the middle part of the duodenal loop, ii) midway between the end point of duodenal loop and Meckel's diverticulum ejunum), and iii) midway between the Meckel's diverticulum and the ileo-cecal junction (ileum). The intestinal segments were flushed with 10% neutral buffered formalin solution and were then used for morphometric analysis. For morphometric analysis, segments were fixed in 10% neutral buffered formalin solution overnight. Intestinal samples were then excised, dehydrated in tissue processing machine (Leica, Japan) and embedded in paraffin wax. Sections of 4 μm were cut from each of the sample, fixed on slides, stained with haematoxylin and eosin, mounted and examined under light microscopes. The morphometric variables examined included: villi height (from the tip of the villi to the villi crypt junction), crypt depth (defined as the depth of the invagination between adjacent villi). The villi height and crypt depth were measured using image analyzer. Values are means from the best 20 villi and only vertically oriented villi and crypts from each slide were measured.

Volatile Fatty Acid (VFA) Determination

The VFA concentration in the feces was determined using the modified method of Jin et al. (1998). One gram of faecal sample (stored at −20° C.) from each sample was weighed in a sampling tube. One mL of 24% metaphosphoric acid diluted in 1.5 M sulphuric acid (Bill) Laboratories, Poole, UK) was added. The mixture was kept at room temperature overnight and centrifuged at 10,000 rpm for 20 min at 4° C. The collected supernatant was kept in a 2-mL screw-capped vial (Kimble Glass Inc., USA). The internal standard 20 mM 4-methyl-valeric acid (Sigma Chemical Co., St. Louis, Mo., USA) was added to the supernatant to achieve 10 mM in the combination and stored at −20° C. until GLC analysis. VFA were separated by a Quadrex 007 Series (Quadrex Corp., New Haven, Conn. 06525 USA) bonded phase fused silica capillary column (15 m, 0.32 mm ID, 0.25 μm film thickness) in a 6890N (Hewlett-Packard, Avondale, Pa.) equipped with a flame ionization detector. The purified nitrogen functioned as a carrier gas with a flow rate of 60 mL/min. The temperature of the injector and detector was 230° C. The column temperature was set at 200° C. in an isothermal status. The commercial standards of 20 mM acetic, and 10 mM each of propionic, butyric, isobutiric, valeric, isovaleric and 4-methyl-valeric acids from Sigma (Sigma chemical Co., St. Louis, Mo., USA) were used as external standards to identify the peaks. The faecal VFA is presented in Table 5. The main VFA was acetic, followed by propionic and butyric but in smaller concentration. The treatments supplemented with 0.4% and 0.3% Com3456 had the highest ($p<0.05$) acid acetic and total VFA level. In contrast, the lowest ($p<0.05$) results were found in −ve control birds. However, no significant difference ($p>0.05$) of acetic acid and total VFA concentration was found among the rest of the treatments. With regard to propionic acid and other VFA, no significant difference ($p>0.05$) was observed among all of the treatments. The butyric acid level of birds fed with 0.1% Com3456 was significantly different ($p<0.05$) with that of treatments supplemented with 0.3%, 0.4% and 0.5% Com3456. However, no significant difference ($p>0.05$) was found among the other 6 treatments. The supplementation of metabolite combinations increased the faecal VFA. There was an increase of VFA in some dosages of Com3456, especially in 0.3% and 0.5% Com3456 at week 3 and 0.4% Com3456 at week 6. One of the main reasons of the increase of VFA in treated birds may be the increase of LAB in treatments supplemented with metabolite combinations as LAB and other gut microbiota ferments various substrates like lactose, biogenic amines and allergenic compounds into short-chain fatty acids and other organic acids and gases (Gibson & Fuller, 2000).

TABLE 5

Villus height and crypt depth in small intestine of treatments supplemented with different metabolite combinations

| Description | | −ve Control | +ve Control | Com3456 | Com246 | Com256 | Com2456 | SEM |
|---|---|---|---|---|---|---|---|---|
| Villus height, μm | Duodenal | 1312.84$^c$ | 1386.58$^b$ | 1486.44$^a$ | 1315.20$^c$ | 1376.6$^{cb}$ | 1406.38$^b$ | 9.90 |
| | Jejunal | 904.42$^c$ | 918.20$^c$ | 1012.80$^{ba}$ | 996.92$^b$ | 1035.40$^a$ | 1003.50$^{ba}$ | 5.10 |
| | Ileal | 554.17$^d$ | 577.50$^{dc}$ | 592.17$^{bc}$ | 641.70$^a$ | 607.80$^b$ | 620.00$^{ba}$ | 4.48 |
| Crypt depth, μm | Duodenal | 157.34$^{dc}$ | 141.64$^e$ | 187.59$^a$ | 173.10$^{ba}$ | 152.40$^{de}$ | 168.63$^{bc}$ | 2.21 |
| | Jejunal | 117.42$^c$ | 173.51$^a$ | 147.80$^b$ | 176.17$^a$ | 162.20$^{ba}$ | 152.60$^b$ | 2.34 |
| | Ileal | 88.00$^{dc}$ | 113.25$^a$ | 97.50$^{bc}$ | 105.40$^{ba}$ | 112.50$^a$ | 80.00$^d$ | 1.67 |

Dietary Treatments[1]

$^{a-e}$Means ± SEM in the same row with common superscript are non-significantly different.
[1]Com3456 is a combination of 4 strains RS5, RI11 RG11 and RG14; Com246 is a combination of TL1, RI11 and RG11; Com256 is a combination of TL1, RI14 and RG11; Com2456 is a combination of TL1, RI11, RG14 and RG11.

Data Analysis

Data were analyzed as a complete randomized design using the General Linear Models procedure of the Statistical Analysis System (SAS, 1998). Duncan Multiple Range Test was used to compare means of treatments. The data were presented as the mean±standard error of the mean (SEM). The experimental units are pens with broiler chickens as experimental subjects. The statistical model is as the following:

$$Y_{ijk} = \mu + \tau_i + \epsilon_{ij} + \delta_{ijk}$$

μ = mean effect
τi = ith treatment effect
εij = random error
δijk = sampling error

The invention claimed is:

1. An animal feed formulation comprising:
bacteriocins produced by *Lactobacillus plantarum*, the *Lactobacillus plantarum* being selected from the group consisting of RI11, RG14, RS5 and RG11 strains or combinations thereof; and
at least one antioxidant and at least one anti-mold compound.

2. The animal feed formulation of claim 1 further comprising at least one component selected from the group consisting of corn, meal, rice bran, wheat pollard, molasses, palm oil, crude coco oil, limestone, monodicalciumphosphate, dicalcium phosphate, salt, lysine, choline chloride, vitamins, minerals, threonine, copper sulfate and DL-methionine.

3. The animal feed formulation of claim 2, wherein the animal feed formulation comprises corn and the corn is yellow corn.

4. The animal feed formulation of claim 2, wherein the animal feed formulation comprises meal and the meal includes soybean and copra meal.

5. The animal feed formulation of claim 2, wherein the animal feed formation comprises palm oil and the palm oil includes refined and crude palm oil.

6. The animal feed formulation of claim 2, further comprising organic acids.

7. The animal feed formulation of claim 6, wherein the organic acids are selected from the group consisting of formic acid, acetic acid and lactic acid.

8. The animal feed formulation of claim 2, further comprising vitamins.

9. The animal feed formulation of claim 8, wherein the vitamins include vitamin B.

10. The animal feed formulation of claim 1, wherein the animal feed formulation increases an animal's total feed intake between 3% and 10%.

11. The animal feed formulation of claim 1, wherein the animal feed formulation increases animal growth between 5% and 7%.

12. The animal feed formulation of claim 1, wherein the animal feed formulation has a conversion rate between 3% and 8%.

13. The animal feed formulation of claim 1, wherein the animal feed formulation reduces faecal enterobacteriaceae count and increase faecal lactic bacteria count in monogastric or non-ruminant animals.

14. The animal feed formulation of claim 1, wherein the animal feed formulation reduces plasma and meat cholesterol in monogastric or non-ruminant animals.

15. The animal feed formulation of claim 1, wherein the animal feed formulation increases villi height of small intestine in monogastric or non-ruminant animals.

16. The animal feed formulation of claim 1, wherein the bacteriocins are present in an amount of 0.1% to 0.5% by dry weight.

17. The animal feed claim 1, wherein the bacteriocins are present in an amount between 0.05% and 0.8%.

18. The animal feed of claim 1, wherein the anti-mold compound is a toxin binder.

19. An animal feed formulation comprising:
bacteriocins, corn, meal, rice bran, wheat pollard, molasses, palm oil, crude coco oil, limestone, monodicalciumphosphate, dicalcium phosphate, salt, lysine, choline chloride, vitamins, minerals, threonine, anti-mold compounds, copper sulfate and DL methionine,
wherein the bacteriocins are provided by *Lactobacillus plantarum*, the *Lactobacillus plantarum* being selected from the group consisting of RI11, RG14, RS5 and RG11 strains or combinations thereof.

* * * * *